United States Patent
Inagaki et al.

(10) Patent No.: US 10,335,084 B2
(45) Date of Patent: Jul. 2, 2019

(54) AUDIO DEVICE

(71) Applicant: KYOCERA CORPORATION, Kyoto (JP)

(72) Inventors: Tomohiro Inagaki, Yokohama (JP); Asao Hirano, Koganei (JP)

(73) Assignee: KYOCERA Corporation, Kyoto (JP)

( * ) Notice: Subject to any disclaimer, the term of this patent is extended or adjusted under 35 U.S.C. 154(b) by 890 days.

(21) Appl. No.: 14/830,472

(22) Filed: Aug. 19, 2015

(65) Prior Publication Data

US 2016/0066851 A1 Mar. 10, 2016

(30) Foreign Application Priority Data

Sep. 8, 2014 (JP) ................ 2014-182377

(51) Int. Cl.
*A61B 5/00* (2006.01)
*H04R 1/02* (2006.01)
*H04R 1/10* (2006.01)
*A61B 5/024* (2006.01)
*H04R 17/00* (2006.01)
*H04R 25/00* (2006.01)
*H04R 5/033* (2006.01)
(Continued)

(52) U.S. Cl.
CPC ........ *A61B 5/6817* (2013.01); *A61B 5/02055* (2013.01); *A61B 5/0295* (2013.01); *A61B 5/02427* (2013.01); *A61B 5/6815* (2013.01); *H04R 1/028* (2013.01); *H04R 1/1041* (2013.01); *H04R 1/1075* (2013.01); *H04R 17/00* (2013.01); *H04R 25/604* (2013.01); *A61B 5/02438* (2013.01); *H04R 1/1008* (2013.01); *H04R 5/0335* (2013.01); *H04R 2225/61* (2013.01)

(58) Field of Classification Search
CPC ................................. A61B 5/6817
See application file for complete search history.

(56) References Cited

U.S. PATENT DOCUMENTS 4,471,258 A * 9/1984 Kumada ........... H04R 17/00
310/345
5,062,432 A * 11/1991 James ............... A61B 5/01
374/E3.009
(Continued)

FOREIGN PATENT DOCUMENTS

JP S58-198329 A 11/1983
JP H09-252496 A 9/1997
(Continued)

OTHER PUBLICATIONS

An Office Action; "Notice of Reasons for Rejection," issued by the Japanese Patent Office dated Feb. 7, 2017, which corresponds to Japanese Patent Application No. 2015-142926 and is related to U.S. Appl. No. 14/830,472; with English language Concise Explanation.
(Continued)

*Primary Examiner* — John R Downey
(74) *Attorney, Agent, or Firm* — Studebaker & Brackett PC

(57) ABSTRACT

There has been no sufficient study to address an issue caused in the use of an open-air type audio device. Therefore, provided is an audio device with an actually useful organism sensor. In particular, the audio device includes an audio unit 10 to externally abut on the ear without being inserted thereinto, and an organism sensor unit 70 to be inserted into the ear.

13 Claims, 8 Drawing Sheets

(51) Int. Cl.
*A61B 5/0205* (2006.01)
*A61B 5/0295* (2006.01)

(56) References Cited

U.S. PATENT DOCUMENTS

| | | | |
|---|---|---|---|
| 6,808,473 B2* | 10/2004 | Hisano | A63B 71/0686 |
| | | | 482/8 |
| 8,189,846 B2* | 5/2012 | Tiscareno | H04R 1/1016 |
| | | | 381/322 |
| 8,647,270 B2 | 2/2014 | LeBoeuf et al. | |
| 8,700,111 B2 | 4/2014 | LeBoeuf et al. | |
| 8,737,667 B2* | 5/2014 | Oh | A61B 5/6898 |
| | | | 379/430 |
| 8,886,269 B2 | 11/2014 | LeBoeuf et al. | |
| 8,923,941 B2 | 12/2014 | LeBoeuf et al. | |
| 8,929,966 B2 | 1/2015 | LeBoeuf et al. | |
| 8,934,952 B2 | 1/2015 | LeBoeuf et al. | |
| 8,961,415 B2 | 2/2015 | LeBoeuf et al. | |
| 8,989,830 B2 | 3/2015 | LeBoeuf et al. | |
| 9,131,312 B2 | 9/2015 | LeBoeuf et al. | |
| 9,301,696 B2 | 4/2016 | LeBoeuf et al. | |
| 9,314,167 B2 | 4/2016 | LeBoeuf et al. | |
| 9,289,135 B2 | 5/2016 | LeBoeuf et al. | |
| 2002/0143242 A1* | 10/2002 | Nemirovski | H04B 1/3877 |
| | | | 600/300 |
| 2006/0132382 A1 | 6/2006 | Jannard | |
| 2007/0057601 A1* | 3/2007 | Kawase | H04R 17/00 |
| | | | 310/328 |
| 2008/0137883 A1* | 6/2008 | Araki | H04M 1/605 |
| | | | 381/107 |
| 2008/0220535 A1 | 9/2008 | LeBoeuf et al. | |
| 2008/0319325 A1* | 12/2008 | Tatara | A61B 5/021 |
| | | | 600/480 |
| 2009/0112071 A1 | 4/2009 | LeBoeuf et al. | |
| 2010/0217098 A1 | 8/2010 | LeBoeuf et al. | |
| 2010/0217099 A1 | 8/2010 | LeBoeuf et al. | |
| 2010/0217100 A1 | 8/2010 | LeBoeuf et al. | |
| 2010/0217102 A1* | 8/2010 | LeBoeuf | A61B 5/00 |
| | | | 600/310 |
| 2012/0283578 A1 | 11/2012 | LeBoeuf et al. | |
| 2013/0131519 A1* | 5/2013 | LeBoeuf | A61B 5/0077 |
| | | | 600/476 |
| 2014/0135596 A1 | 5/2014 | LeBoeuf et al. | |
| 2014/0140567 A1 | 5/2014 | LeBoeuf et al. | |
| 2014/0171755 A1 | 6/2014 | LeBoeuf et al. | |
| 2014/0171762 A1 | 6/2014 | LeBoeuf et al. | |
| 2014/0180039 A1 | 6/2014 | LeBoeuf et al. | |
| 2014/0243620 A1 | 8/2014 | LeBoeuf et al. | |
| 2014/0288395 A1 | 9/2014 | LeBoeuf et al. | |
| 2014/0323830 A1 | 10/2014 | LeBoeuf et al. | |
| 2015/0032009 A1 | 1/2015 | LeBoeuf et al. | |
| 2015/0073236 A1 | 3/2015 | LeBoeuf et al. | |
| 2015/0105633 A1 | 4/2015 | LeBoeuf et al. | |
| 2015/0126824 A1 | 5/2015 | LeBoeuf et al. | |
| 2015/0131837 A1 | 5/2015 | LeBoeuf et al. | |
| 2015/0157222 A1 | 6/2015 | LeBoeuf et al. | |
| 2015/0289818 A1 | 10/2015 | LeBoeuf et al. | |
| 2015/0342467 A1 | 12/2015 | LeBoeuf et al. | |
| 2016/0128637 A1 | 5/2016 | LeBoeuf et al. | |

FOREIGN PATENT DOCUMENTS

| | | | |
|---|---|---|---|
| JP | 10117397 A * | 5/1998 | |
| JP | 2006-212178 A | 8/2006 | |
| JP | 2006-304147 A | 11/2006 | |
| JP | 2005-348193 A | 12/2006 | |
| JP | 2008211642 A * | 9/2008 | |
| JP | 2012-518515 A | 8/2012 | |
| WO | 2015/162913 A1 | 10/2015 | |

OTHER PUBLICATIONS

The extended European search report issued by the European Patent Office dated Feb. 23, 2016, which corresponds to European Patent Application No. 15181659.2-1910 and is related to U.S. Appl. No. 14/830,472.

* cited by examiner

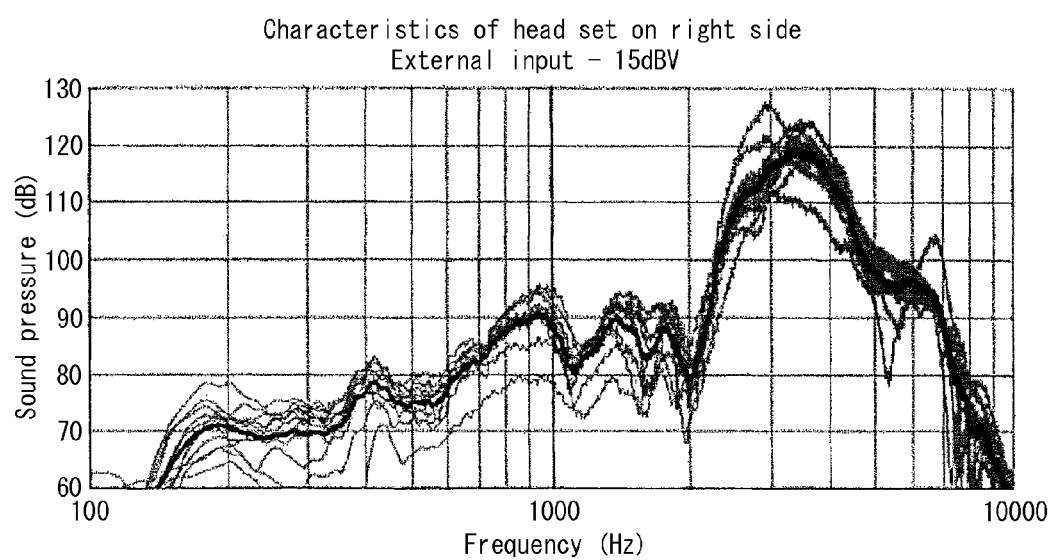

AUDIO DEVICE

TECHNICAL FIELD

This disclosure relates to an audio device with an organism sensing function.

BACKGROUND

Lately, an audio device having an earphone with a sensor for measuring a volume of blood flow, a blood pressure and the like has been developed. Also, there has been known an open-air type hearing aid.

CITATION LIST

Patent Literatures

PLT 1: US2008220535A1
PLT2: US2012283578A1
PLT3: JP2006304147A

SUMMARY

However, there has been no study to address an actual issue of the earphone and the like having an organism sensor mounted therein.

For example, an issue caused in using an open-air type audio device has not been sufficiently studied.

Therefore, it could be helpful to provide an audio device with an organism sensing function that is actually useful.

The audio device according to the present disclosure includes an audio unit to externally abut on the ear without being inserted thereinto and an organism sensor unit to be inserted into the ear.

The audio device according to the present disclosure considers actual issues and thus is useful.

BRIEF DESCRIPTION OF THE DRAWINGS

In the accompanying drawings:
FIG. 9 is a diagram illustrating measured data of acoustic characteristics.

DETAILED DESCRIPTION

Hereinafter, an embodiment will be described.
An audio device according to one of the embodiment is, for example, a hearing aid or a headphone and generally includes an audio unit 10, an organism sensor unit 500, and a support 60 for supporting the audio unit 10 and the organism sensor unit 500.

Figure 2:
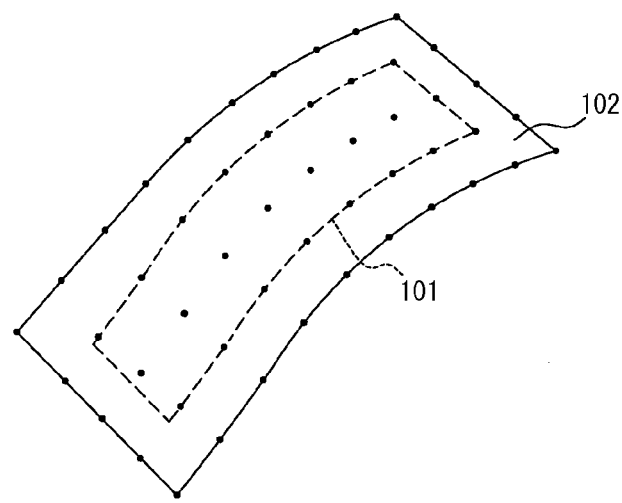
FIG. 2 is a schematic diagram illustrating curve of a panel of the audio device and a piezoelectric element.

The audio unit 10 includes a piezoelectric element 101 that curves and a panel 102 that vibrates when directly bent by the piezoelectric element 101. FIG. 2 is a diagram schematically illustrating a state of the panel 102 bent by the piezoelectric element 101. The panel 102, when directly bend by the piezoelectric element 101, vibrates and widely curves in a central area thereof in a manner protruding from both ends thereof. The audio unit 10 functions to provide a user with a human body vibration sound caused mainly by vibration. Depending on a size of the panel, an air conduction sound may be generated. The air conduction sound is a sound that is delivered to the user's auditory nerve when air vibration caused by vibration of a substance travels through the external ear canal and vibrates the ear drum. The human body vibration sound is a sound that is delivered to the user's auditory nerve via a part of the user's body (for example, the cartilage of the external ear) in contact with a vibrating substance. The human body vibration sound may contain a component that changes from the vibration to the air conduction inside the external ear canal. We have preliminarily found in a research that, even when the panel 102 is small, vibration of the ear causes at least a 6th harmonic sufficiently higher than a background noise at least at three positions in the panel. When the harmonic components are provided together, regardless of the size of the panel 102 (for example, a rectangular shape of 3 cm in length and 1 cm in width or smaller), the sound becomes enough loud to be heard. The human body vibration sound contributes especially to articulation and thus is suitable for a person with geriatric defective hearing who has a difficulty in hearing a high pitch sound.

The piezoelectric element 101 is an element that, upon application of an electric signal (a voltage), contracts or curves (bends) according to an electromechanical coupling factor of a material thereof. The piezoelectric element 101 is directly attached to the panel 102 via a double-sided tape. The piezoelectric element may be made of, for example, ceramics or crystal. The piezoelectric element 101 may be a unimorph, a bimorph, or a laminated piezoelectric element. The laminated piezoelectric element includes a laminated unimorph element in which the unimorphs are laminated (for example, approximately 16 to 100 layers thereof) or a laminated bimorph element in which the bimorphs are laminated (for example, approximately 16 to 48 layers thereof). The laminated piezoelectric element includes a plurality of dielectric layers made of, for example, PZT (lead zirconate titanate) and electrode layers disposed therebetween. In response to the application of the electric signal (the voltage), the unimorph contracts, while the bimorph bends.

The panel 102 is made of, for example, a hard material such as glass and sapphire, or a synthetic resin such as acryl and polycarbonate. Preferably, the panel 102 is in a plate shape, and hereinafter the panel 102 is assumed as such. For example, the panel is approximately 2 cm to 5 cm in length and 0.5 cm to 2 cm in width. The piezoelectric element 102 is directly attached to the panel 102 via the double-sided tape and the like.

The microphone 20 collects a sound from a sound source, in particular, a sound that reaches near the user's helix. Since the microphone 20 is behind the helix and thus unlikely to collect a sound leaking from the external ear canal (i.e., unlikely to cause howling), the microphone 20 may easily reproduce a natural sound to the user.

One microphone unit may be provided to the audio unit 10 on both a left side and a right side. One microphone may generate a signal to be shared by the audio units on the left side and the right side.

Note that the microphone is not necessary when an audio device does not need a function to collect and provide an ambient sound. It is a matter of course that the microphone may be used for an input of a telephone call. An exterior audio signal or an audio signal stored in an internal storage area needs to be input to a controller 30.

Figure 3:
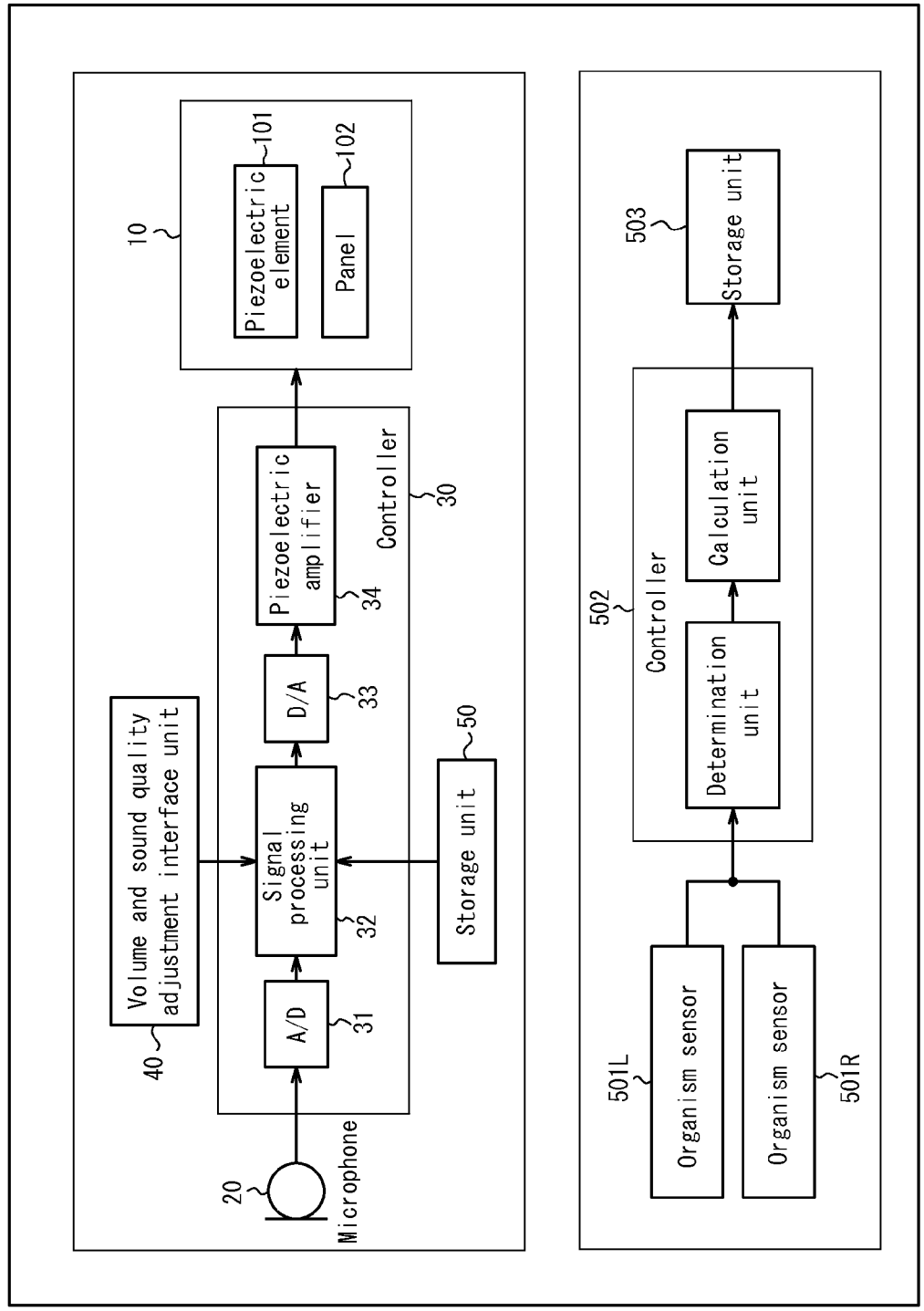
FIG. 3 is a block diagram of the audio device.

FIG. 3 illustrates an example of a block diagram. The controller (IC) 30 carries out various control of the audio device 1. The controller 30 applies a predetermined electric signal (a voltage according to a sound signal) to the piezoelectric element 101. In particular, the controller 30 controls an A/D converter 31 to convert the sound signal collected by the microphone unit 20 into a digital signal. Then, a signal processing unit 32, based on information on volume and sound quality provided from a volume adjustment interface unit 40 and also on information stored in a storage unit 50, outputs a digital signal for driving the audio unit 10. A D/A converter 33 converts the digital signal into an analogue electric signal, which is then amplified by a piezoelectric amplifier 34 and applied to the piezoelectric element 101. The voltage applied to the piezoelectric element 101 by the controller 30 may be higher than, for example, an applied voltage of an air conduction earphone speaker for delivering the air conduction sound. Thereby, the panel 102 generates sufficient vibration and thus the human body vibration sound that is delivered via a part of the user's body. A level of the voltage to be applied may be appropriately adjusted according to fixing strength of the panel 102 or performance of the piezoelectric element 101. When the controller 30 applies the electric signal to the piezoelectric element 101, the piezoelectric element 101 curves in a longitudinal direction thereof.

At this time, the panel 102 having the piezoelectric element 101 attached thereto deforms according to the contraction or bend of the piezoelectric element 101 and vibrates. The panel 102 curves due to the contraction or bend of the piezoelectric element 101. The panel 102 is directly bent by the piezoelectric element 101. Here, "the panel 102 is directly bent by the piezoelectric element 101" is different from a phenomenon in which, as employed in a conventional panel speaker, inertial force of a piezoelectric actuator having the piezoelectric element 101 disposed inside a casing vibrates a particular area of the panel 102 and deforms the panel 102. "The panel 102 is directly bent by the piezoelectric element 101" is a phenomenon in which the contraction or bend (curve) of the piezoelectric element 101 directly bends the panel 102 via a joining member.

As described above, since the panel 102 vibrates, when the panel 102 is in contact with the tragus, the human body vibration sound is generated via the tragus. Preferably, the panel 102 vibrates having areas near both ends thereof functioning as a joint and the center thereof as the flat, in such a manner that an area near the center of the panel 102 abuts on the tragus and the antitragus. Thereby, the vibration of the panel 102 may be efficiently delivered to the tragus and the antitragus.

Figure 1:
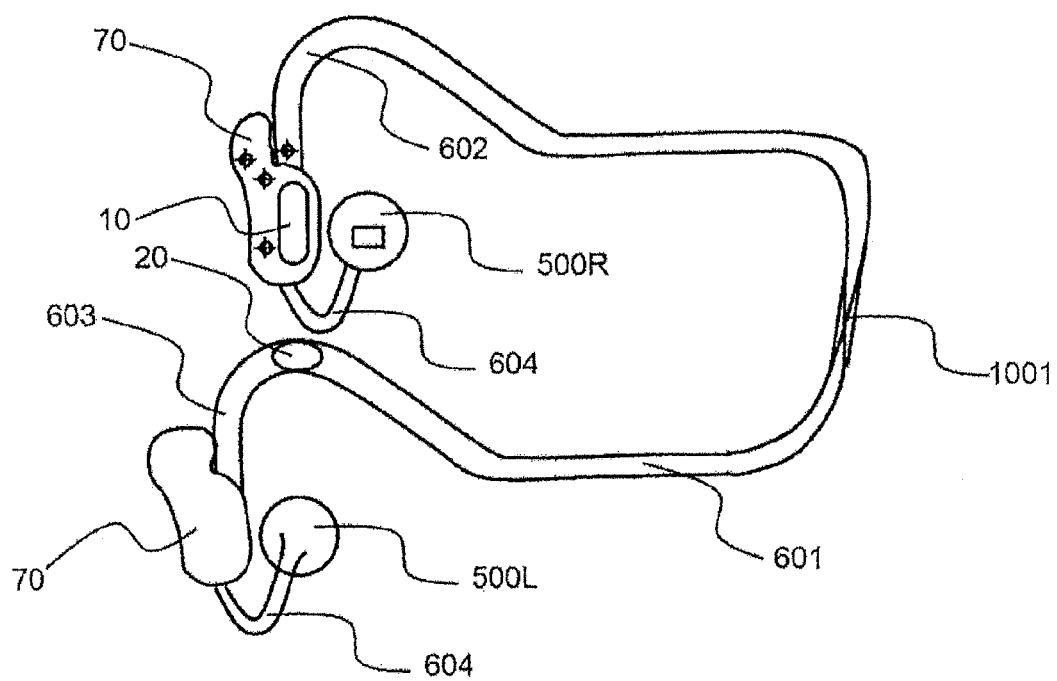
FIG. 1 is an external view of an audio device according to one embodiment.

As illustrated in FIG. 1, the support 60, at both ends thereof, supports a housing unit 70. Further, the housing unit 70 supports the audio unit 10 at a position opposite to the ear.

The support 60 supports the audio unit 10 and the organism sensor unit 500. Thereby, the audio unit 10 abuts on the ear. Here, on the user's ear, the audio unit 10 may abuts on, for example, the tragus or the antitragus. According to the present embodiment, hereinafter, it is assumed that the audio unit 10 abuts on the tragus. The organism sensor unit 500 is supported by a joint portion 604 extending from a bottom of the housing unit 70 at a position blocking the user's ear shell. The joint portion 604 is constituted by using a member such as a flat spring having appropriate elasticity. The joint portion 604 may be made of metal or resin, as a matter of course. Inside the joint portion 604, a wire 510 is provided to supply an output signal from the organism sensor unit 500 and supply power to the organism sensor unit 500.

The support 60 includes an arm portion 601 in a semicircular shape extending along the user's occipital region. The arm portion 601 may be designed to allow adjustment of pressure approximately between 0.1 N to 10 N when the housing unit 70 abuts on, for example, the tragus. The arm portion 601 may be made of a metal spring curved into a predetermined shape and coated with resin, or a resin spring and the like, and has appropriate elasticity.

Figure 8:
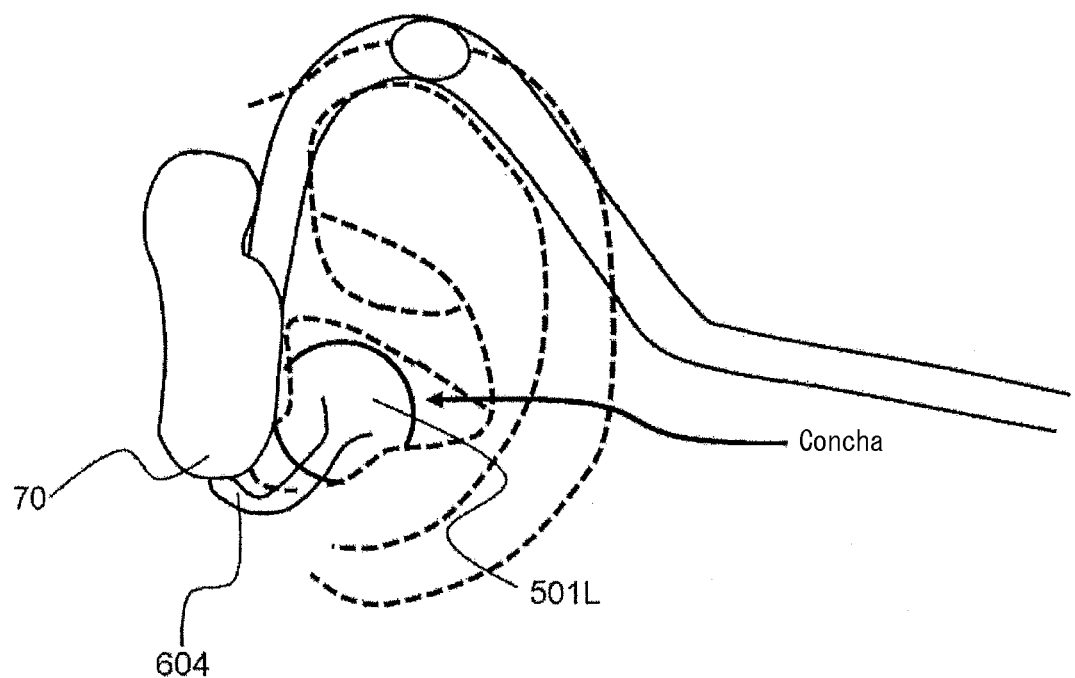
FIG. 8 is a diagram illustrating a state of wearing the audio device.

The support 60 includes a pair of ear hooking portions 602 formed continuously from the arm portion 601. The ear hooking portions 602, as illustrated in FIG. 8, curve to hang on a part of the user's helix. The ear hooking portions 602 may be integrally formed with the arm portion 601.

Each of the ear hooking portions 602 of the support 60 is provided with the microphone 20. Although it is preferable that two microphones are provided for each of the left ear and the right ear, one microphone may be provided for either one of the ears. The signal from the microphone 20, through a signal wiring (not shown) disposed inside the support 60 (the ear hooking portions 602 and a support portion 603), is input to the controller 30 described later.

The support 60, at a distal end of the ear hooking portion 602, is provided with the support portion 603 for supporting the housing unit 70. The support portion 603 supports the housing unit 70 in such a manner that the panel 102 disposed on the housing unit 70 abuts on the user's ear.

The housing unit 70 is supported by the support portion 603 of the support 60 and includes a substrate 702 and the like thereinside. The following is a detailed description of the housing unit 70 and the audio unit 10 with reference to FIG. 4 by way of example.

Figure 4:
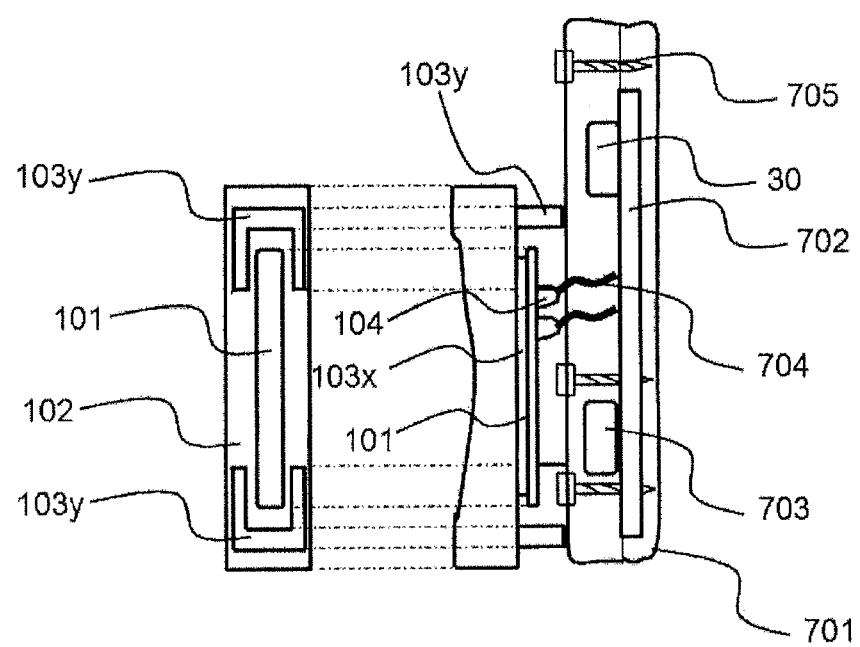
FIG. 4 is a diagram illustrating a cross-sectional view of an audio unit and a housing unit of the audio device in a thickness direction and a bottom view of the audio unit.

FIG. 4 is a cross-sectional diagram of the audio unit 10 and the housing unit 70 viewed in a thickness direction. As described above, the audio unit 10 includes the piezoelectric element 101 and the panel 102. Preferably, the piezoelectric element 101 is in a panel shape as illustrated in FIG. 4.

The piezoelectric element 101 is attached to the panel 102 via a joint member 103x. The joint member 103x is provided between a principal plane of the piezoelectric element 101 and a principal plane of the panel 102. The joint member 103x is preferably a non-thermosetting adhesive or the double-sided tape. The double-sided tape may be, for example, a cloth impregnated with adhesive resin.

Preferably, the principal plane of the panel 102 is in size 0.8 to 10 times larger than the principal plane of the piezoelectric element 101. When the size of the principal plane of the panel 102 is within a range of 0.8 to 10 times of the size of the principal plane of the piezoelectric element 101, the panel 102 may deform according to the contraction or bend of the piezoelectric element 101 and, also, a sufficient area to come into contact with the user's ear may be ensured. More preferably, the size of the panel is, for example, 0.8 to 5 times of the size of the piezoelectric element.

Also, the panel 102, on the principal plane on an ear side, may have a concave shape. Thereby, the panel 102 may be more easily contact the tragus that is protruding, in comparison with the panel 102 with a flat principal plane. That is, the panel 102 having the concave shape is effective in preventing displacement thereof.

On a rear side of the panel 102 (on a side opposite to the housing unit 70), a pair of double-sided tapes 103y are attached. These double-sided tapes 103y attach the panel 102 to a principal plane of the housing unit 70. Thereby, the panel 102 is attached to the housing unit 70. The double-sided tape 103y is provided at either end of the piezoelectric element 101. Since the double-sided tape 103y is not provided to the piezoelectric element 101 at any other positions including the center area than each end of the piezoelectric element 101, sufficient vibration of the piezoelectric element 101 with low power consumption may be ensured at the center thereof. Note that, when the piezoelectric element 101 sufficiently strongly vibrates, the double-sided tape 103y may be provided in the entire area of the panel 102 in order to attach the panel 102 to the housing unit 70.

Preferably, the double-sided tape 103y is attached in a U-shape or a C-shape along three ends of the piezoelectric element 101, from a viewpoint of reinforcing the adhesion while efficiently using the small area of the panel 102. Thereby, the double-sided tape 103y is unlikely to inhibit the bend of the panel 102.

On a rear side (on a side opposite to the housing unit 70) of the piezoelectric element 101, a pair of solders 104 are formed, to which a wire 704 is joined connecting to the substrate 702 in the housing unit 70 described later.

The housing unit 70 includes a housing 701, the substrate 702, a battery 703, the wire 704, and a screw 705. Further, the housing 70 includes the controller (IC) 30 built therein.

The housing 701 is made of, for example, plastics. In particular, the housing 701 is obtained by molding a resin material such as polycarbonate resin and amine-based resin. Alternatively, a material in which synthetic resin having glass fiber weaved therein (for example, Reny (registered trademark) produced by Mitsubishi Gas Chemical Company, Inc.) may be used. The material of the housing 701 needs to be as light as possible so as ease the burden on the helix, as well as to be sufficiently strong against an impact of falling and the like. However, when the material is too light and thin, a resonance is easily generated, causing energy loss. Accordingly, a material and weight of the housing 701 is determined in consideration of both lightness and strength. That is, from a viewpoint of vibration, a material having rigidity as high as possible is preferably used. From this point of view, the housing 701 may be made of thick metal.

The housing 701 is one casing made up of a pair of members bolted together using screws 705. When the battery 703 is not rechargeable, the members are preferably bolted together, rather than being bonded together, so as to allow replacement of the battery 703.

The substrate 702 inside the housing 701 is electrically connected to the controller 30 and the piezoelectric element 101 via the solders 104 and the wire 704. Also, the substrate is provided with the battery 703 mounted thereon.

FIG. 8 is a diagram illustrating a state in which the user is wearing the audio device 1 according to one embodiment on the ear. According to the audio device 1, the audio unit 10 externally abuts on the ear near the user's tragus and antitragus and delivers the vibration thereto, thereby providing the sound to the user. In an example illustrated in FIG. 5, the audio unit 10 externally abuts on the user's tragus. It is a matter of course that the audio unit 10 may abuts on either one of, or both of, the ears.

Preferably, the audio unit 10 applies a pressure of 0.1 N to 3 N to the user's ear. When the audio unit 10 applies a pressure within a range of 0.1 N to 3 N, the vibration of the audio unit 10 is sufficiently delivered to the ear. Also, when the pressure is equal to or lower than 3 N, the audio device 1 hardly makes the user feel tired after wearing the audio device 1 for many hours and is capable of maintaining wearing comfort. Further, the tragus being slightly flattened does not block the external ear canal and thus is less likely to cause an ear-stuffed feeling.

Now, acoustic characteristics of the audio device 1 according to one embodiment will be described with reference to FIG. 9. FIG. 9 illustrates measured data of acoustic characteristics of the audio unit 10 on the right side of the audio device 1. FIG. 9 illustrates data of 12 samples and a mean value thereof. As can be seen in the figure, with respect to an external input at 15 dBV, sufficiently good acoustic characteristics are shown in each frequency band from 200 Hz to 8 kHz. Especially between 3 kHz and 4 kHz, a high sound pressure was obtained, which is effective also for a hearing-impaired person who speaks a language other than Japanese, such as English and the like. Further, the audio device 1 has a wide coverage of the frequency band and thus may be preferably used as the earphone. Note that the audio device 1 illustrated in FIG. 6 employs a low-pass filter for gradually attenuating a signal at 8 kHz or over.

When the low-pass filter or the like is not employed, the piezoelectric element 101 may vibrate in response to a sound in an ultrasonic frequency band such as, for example, 40 kHz. Therefore, the audio device 1 may also function as an audio device for generating various ultrasonic waves.

Figure 5:
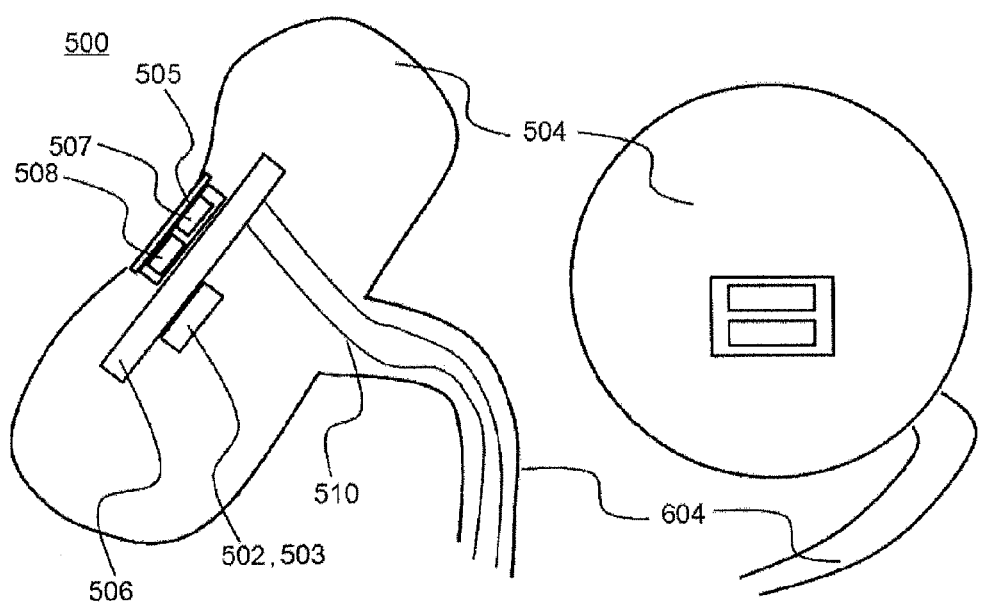
FIG. 5 is a cross-sectional view and an appearance view of an organism sensor unit of the audio device.
Figure 6:
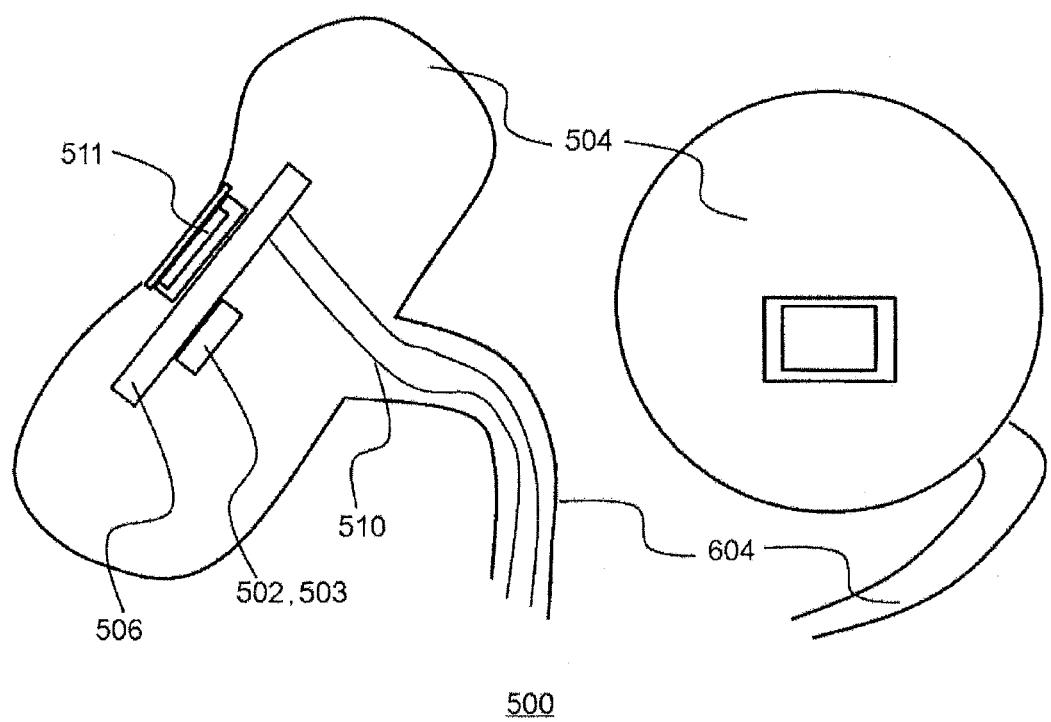
FIG. 6 is a cross-sectional view and an appearance view of another organism sensor unit of the audio device.

FIG. 3 illustrates a block diagram of the organism sensor unit 500. The organism sensor unit 500 according to the present embodiment, as illustrated in FIG. 5 and FIG. 6, by using organic sensors 501L and 501R (a light reception unit 508 and a light emission unit 507) mounted in a housing 504 to be inserted into the ear, measures, for example, a user's pulse. The light emission unit 507 and the light reception unit 508 of the organic sensors 501L and 501R are arranged in parallel having a light shielding wall therebetween inside the housing 504. A light transmission panel 505 is disposed on the organic sensors for a protective purpose, whereby the housing 504 is sealed.

In order to measure the pulse, the light emission unit 507 uses a blue (a wavelength: 400 to 430 nm) or a green (the wavelength: 500 to 550 nm) LED or laser. The blue light and the green light with wavelengths described above are easily absorbed by hemoglobin. Therefore, an amount of the light absorbed increases in proportion to a volume of blood flow, and an output to the light reception unit 508 becomes weaker in proportion thereto. Alternatively, a red light (the wavelength: 630 to 650 nm) LED or the laser may be used. In this case, since the hemoglobin reflects an infrared light, an amount of the light reflected increases in proportion to the volume of blood flow, and the output to the light reception unit 508 becomes stronger in proportion thereto. As the light reception unit 508, a photodiode corresponding to the wavelength is used.

In order to measure the volume of blood flow, on the other hand, for example, red (the wavelength: 1.31 μm or 1.55 μm) laser is used so as to detect a relative volume of blood flow from a phase difference of the frequency caused by a Doppler shift.

The housing 504 includes the substrate 506 and the controller 502 therein. The controller 502 mounted on the substrate 506 may include a determination unit for controlling light emission timing of the light emission unit 507 to the light reception unit 508 as well as for determining an error or a noise signal based on a signal of the light reception unit 508, and also a calculation unit for calculating the pulse and the volume of blood flow. Sampling is carried out at intervals of 0.005 to 0.1 second. The determination unit determines that an error has occurred when detecting a high frequency that cannot be generated in the human body.

When the organism sensor unit 500 according to another embodiment is a sensor for measuring the volume of blood flow, the laser for emitting, for example, the red light (the wavelength: 1.31 µm or 1.55 µm) is used to detect the relative volume of blood flow from the phase difference of the frequency caused by the Doppler shift.

The controller 502 provided inside the housing 504, similarly to the sensor for measuring the pulse, controls the light emission timing of the light emission unit 507 to the light reception unit 508 as well as for determining an error or the noise signal based the signal of the light reception unit 508, and the calculation unit for calculating the volume of blood flow. Sampling is carried out at intervals of 0.005 to 0.1 second.

When both a sensor for measuring the pulse and a sensor for measuring body temperature are provided, for example, the organism sensor 501L and an organism sensor 501R may function as a pulse sensor and a body temperature measurement sensor 511, respectively. It is a matter of course that a combination of the blood flow sensor and the pulse sensor or a combination of the blood flow sensor and the body temperature sensor may be used. The body temperature measurement sensor 511 measures the body temperature by, for example, detecting the infrared light travelling from the external ear canal toward outside the ear. Similarly to the example described above, the housing 504 includes the substrate 506 and the controller 502 therein. The controller 502 mounted on the substrate 506 controls an operation of the light reception unit for measuring the body temperature and manages data of the body temperature.

Biometric data from each of the organism sensors are stored in the storage unit 503. Although the storage unit 503 is provided separately from the storage unit 50 that is used for the audio function in FIG. 3, the storage unit 50 may also function as the storage unit 503. The biometric data stored in the storage unit 503 may be externally provided as necessary via a communication unit 1001 and the like.

Next, with reference to FIG. 7, another variation of a configuration of the sensor will be described.

Figure 7:
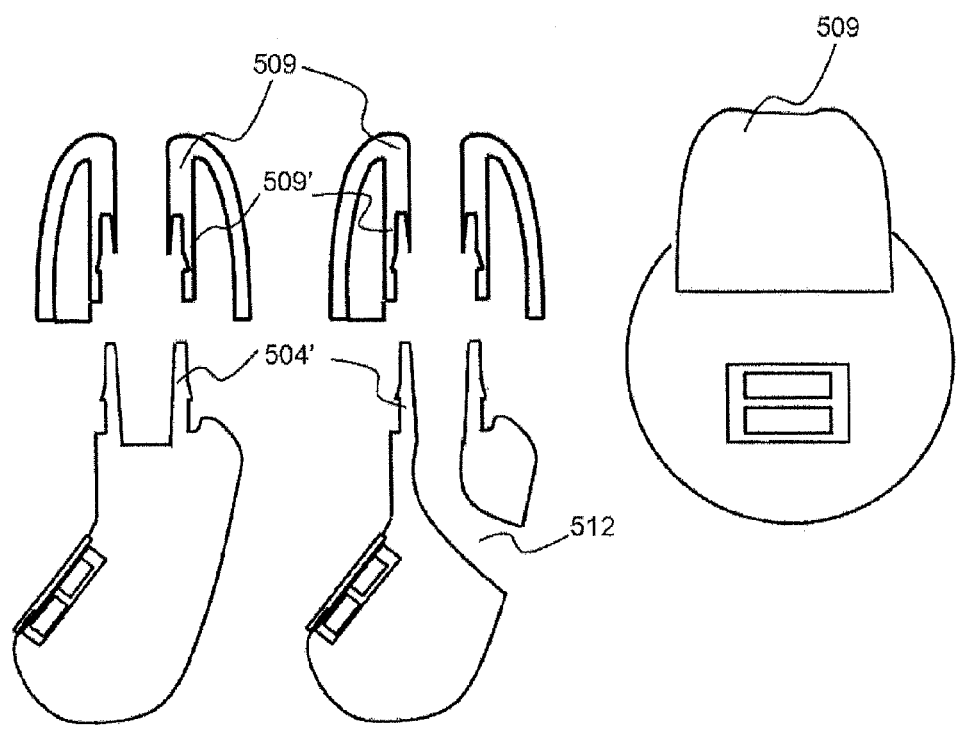
FIG. 7 is a cross-sectional view and an appearance view of an organism sensor unit according to another embodiment.

In FIG. 7, the organism sensor unit 500 includes an insertion unit 509 to be inserted into the external ear canal, which is different from the embodiment illustrated in FIG. 5 and FIG. 6. Therefore, the housing 504 is provided with an engaging unit 504' that is engaged with an engaged portion 509' provided to the insertion unit 509. The insertion unit 509 is made of rubber with Shore hardness of, for example, approximately 30 to 60. Alternatively, the insertion unit 509 may be made of a molded hard polyimide resin. The housing 504 may have a vent (an air hole) 512 so as to reduce the ear-stuffed feeling.

FIG. 8 illustrates a diagram of an example of the wearing state of the audio device 1.

The housing 504 of the organism sensor 500 is placed in such a manner as to face the concha inside the ear. The light emission unit 507 emits the light toward the concha. The light is unlikely to leak outside. A rear side of the housing 504 (outside the ear) abuts on a rear side of the tragus and a rear portion of the antitragus, whereby the housing 504 is held inside the ear. On the other hand, a front side of the housing 504 faces the concha (and may abut on the concha). A space surrounded by the concha and the front side of the housing 504, because of a peripheral portion of the housing 504, is unlikely to receive external light. Therefore, the external light is unlikely to reach the light reception unit 508, and reliability of the measurement of the sensor may be easily improved.

Also, the audio unit 10 abuts on the tragus and, by vibrating the internal wall of the external ear canal, may deliver the air conduction sound. At this time, when the audio unit 10 and the organism sensor 500 sandwich the tragus from inside and outside the ear, the delivery of the vibration is more likely to be ensured.

Next, an example of use when the organization sensor unit 500 includes a combination of the body temperature sensor and the pulse sensor will be described.

First, power of the sensors is turned on, and the pulse and the body temperature are measured simultaneously or in series. Next, the organism sensors obtain the data. Then, it is determined that whether the body temperature is at a threshold or higher (for example, 38° C. degrees or higher) and, simultaneously, whether the pulse is at a threshold (for example, 10% of, or lower than, the pulse in a wakeful state) or less. In this case, the audio unit 10, for example, may issue notification of a possibility of heat stroke. When the audio device includes the communication unit 1001, the communication unit 1001 may transmit, to a registered particular receiver, notification of that the measured person is having the heat stroke or various measured organism data (the pulse, the temperature, and the volume of blood flow). The registered particular receiver may be a user's doctor or nurse and the like.

The communication unit 1001 may employ a conventionally known communication method such as, for example, one in accordance with LTE and the like or Wi-Fi. Although in FIG. 1 the communication unit 1001 is disposed on the rear side of the support 60, i.e., at a position opposite to the occipital region, the location of the communication unit 1001 is not limited thereto.

Also, although in the present embodiment the audio device 1 is the hearing aid, the audio device 1 is not limited thereto. For example, the audio device 1 may be a music player, in which case the microphone 20 may be omitted. Also, the audio device 1 may reproduce music based on music data stored in an internal memory thereof, or based on music data stored in an external server via the network. Further, the audio device 1 may store a synthesized voice or an alarm sound for warning about the heat stroke as described above by way of example.

Although the present disclosure has been described based on the figures and the embodiment, it is to be understood that various modifications and changes may be implemented based on the present disclosure by those who are ordinarily skilled in the art. Accordingly, such modifications and changes are included in a scope of the present disclosure. For example, a function and the like included in each means, unit and the like may be rearranged without logical inconsistency, so as to combine a plurality of means or units together or to divide them.

The invention claimed is:

1. An audio device comprising:
   an audio unit to externally abut on an ear without being inserted into the ear; and
   an organism sensor unit to be inserted into the ear, wherein the audio unit includes a piezoelectric element, and a panel directly attached to the piezoelectric element, and the panel delivers sound by being bent directly by the piezoelectric element, the organism sensor unit is inserted into a concha, the audio unit externally abuts a tragus, wherein the audio unit and the organism sensor unit sandwich the tragus, the organism sensor unit is provided with a light emission unit and a light reception unit, and the light emission unit emits light to the concha.

2. The audio device according to claim 1, wherein the audio device externally abuts on a tragus or an antitragus.

3. The audio device according to claim 1, wherein the organism sensor unit measures a pulse, a volume of blood flow, or body temperature.

4. The audio device according to claim 1, wherein the organism sensor unit is provided with a pair of sensors including a left ear sensor and a right ear sensor.

5. The audio device according to claim 1, wherein the audio unit is provided with a pair of audio units including a left ear audio unit and a right ear audio unit.

6. The audio device according to claim 4, wherein the pair of sensors measure organism data.

7. The audio device according to claim 6, further comprising a communication unit for externally transmitting the organism data.

8. The audio device according to claim 6, wherein when a possibility of a user's health problem is detected from the organism data, the audio unit notifies accordingly.

9. The audio device according to claim 1, wherein the organism sensor unit is provided with an insertion unit to be inserted into an external ear canal.

10. The audio device according to claim 1, wherein the organism sensor is provided with a vent for allowing an external ear canal to communicate with outside.

11. The audio device according to claim 6, wherein the organism data is pulse.

12. The audio device according to claim 6, wherein the organism data is volume of blood flow.

13. The audio device according to claim 6, wherein the organism data is temperature.

* * * * *